(12) United States Patent
Mizuki et al.

(10) Patent No.: US 9,169,274 B2
(45) Date of Patent: Oct. 27, 2015

(54) PYRENE DERIVATIVE AND ORGANIC ELECTROLUMINESCENT ELEMENT USING THE SAME

(75) Inventors: Yumiko Mizuki, Sodegaura (JP);
Masahiro Kawamura, Sodegaura (JP);
Yuichiro Kawamura, Sodegaura (JP);
Hiroyuki Saito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 209 days.

(21) Appl. No.: 13/389,294

(22) PCT Filed: Dec. 20, 2010

(86) PCT No.: PCT/JP2010/007362
§ 371 (c)(1),
(2), (4) Date: Mar. 13, 2012

(87) PCT Pub. No.: WO2011/077690
PCT Pub. Date: Jun. 30, 2011

(65) Prior Publication Data
US 2012/0248420 A1  Oct. 4, 2012

(30) Foreign Application Priority Data
Dec. 21, 2009  (JP) .................. 2009-289734

(51) Int. Cl.
*H01L 51/54* (2006.01)
*C07F 7/08* (2006.01)
*H01L 51/00* (2006.01)
*C09K 11/06* (2006.01)
*H05B 33/10* (2006.01)
*H01L 51/50* (2006.01)

(52) U.S. Cl.
CPC .............. *C07F 7/0809* (2013.01); *C09K 11/06* (2013.01); *H01L 51/0054* (2013.01); *H01L 51/0094* (2013.01); *H05B 33/10* (2013.01); *C09K 2211/1007* (2013.01); *C09K 2211/1011* (2013.01); *H01L 51/5012* (2013.01)

(58) Field of Classification Search
CPC .............. C07F 7/0809; H01L 51/0054; H01L 51/0094; H01L 51/5012; C09K 11/06; C09K 2211/1011; C09K 2211/1007; H05B 33/10
See application file for complete search history.

(56) References Cited

U.S. PATENT DOCUMENTS

| | | | |
|---|---|---|---|
| 7,060,370 B2 | 6/2006 | Kinoshita et al. | |
| 7,232,619 B2 | 6/2007 | Nomura et al. | |
| 2004/0076853 A1* | 4/2004 | Jarikov ................ | 428/690 |
| 2004/0137270 A1 | 7/2004 | Seo et al. | |
| 2005/0236977 A1 | 10/2005 | Yamada et al. | |
| 2007/0114917 A1* | 5/2007 | Funahashi et al. ........ | 313/504 |
| 2008/0004445 A1 | 1/2008 | Hosokawa et al. | |
| 2009/0096356 A1 | 4/2009 | Murase et al. | |

FOREIGN PATENT DOCUMENTS

| | | |
|---|---|---|
| CN | 1535089 A | 10/2004 |
| CN | 101258221 A | 9/2008 |
| JP | 2003 234190 | 8/2003 |
| JP | 2005 126431 | 5/2005 |
| JP | 2007 169581 | 7/2007 |
| JP | 2009 4351 | 1/2009 |
| JP | 2011 1475 | 1/2011 |
| KR | 10 2011 0006915 | 1/2011 |

OTHER PUBLICATIONS

U.S. Appl. No. 13/499,303, filed Mar. 30, 2012, Kawamura, et al.
Combined Office Action issued Nov. 15, 2013 in Chinese Patent Application No. 201080029066.3 (with English translation and English translation of category of cited documents).
Extended European Search Report issued Sep. 4, 2013, in European Patent Application No. 10838930.5.
Maeda, H., et al., "UV Absorption and Fluorescence Properties of Pyrene Derivatives Having Trimethylsilyl, Trimethylgermyl, and Trimethylstannyl Groups," Chemistry Letters, No. 12, pp. 1224-1225, (2001).
International Search Report Issued Mar. 15, 2011 in PCT/JP10/07362 Filed Dec. 20, 2010.
U.S. Appl. No. 13/389,142, filed Mar. 13, 2012, Mizuki, et al.

* cited by examiner

*Primary Examiner* — Dawn Garrett
(74) *Attorney, Agent, or Firm* — Oblon, McClelland, Maier & Neustadt, L.L.P.

(57) ABSTRACT

A pyrene derivative represented by the following formula (1); wherein $R_1$ to $R_{10}$ are independently a hydrogen atom, a substituted or unsubstituted aryl group, a substituted or unsubstituted alkyl group, a substituted or unsubstituted cycloalkyl group or a group represented by the following formula (2), at least one of $R_1$ to $R_{10}$ is a group represented by the following formula (2) and at least two of $R_1$ to $R_{10}$ are substituted or unsubstituted aryl group. Provided that in the case where only one of $R_1$ to $R_{10}$ is a group represented by the following formula (2), at least one of the substituted or unsubstituted aryl groups is an aryl group having 10 to 50 carbon atoms. X, Y and Z are independently a substituted or unsubstituted alkyl group, a substituted or unsubstituted aryl group or a substituted or unsubstituted alkoxy group;

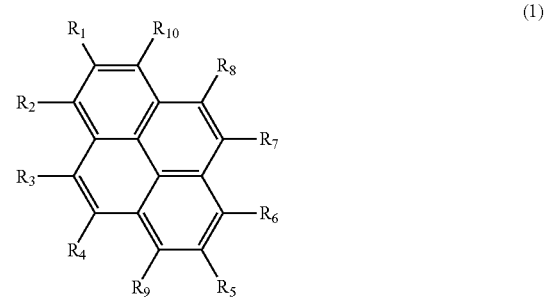

10 Claims, No Drawings

PYRENE DERIVATIVE AND ORGANIC ELECTROLUMINESCENT ELEMENT USING THE SAME

This application is a National Stage of PCT/JP10/007362 filed Dec. 20, 2010 and claims the benefit of JP 2009-289734 filed Dec. 21, 2009.

TECHNICAL FIELD

The invention relates to a pyrene derivative and an organic electroluminescence device using the same. More particularly, the invention relates to a pyrene derivative capable of producing an organic electroluminescence device having a high luminous efficiency.

BACKGROUND ART

An organic electroluminescence (EL) device is a self-emitting device utilizing a principle that a fluorescence material emits light by energy of recombination of holes injected from an anode and electrons injected from a cathode when an electrical field is applied. Such an organic EL device is provided with a pair of electrodes of an anode and a cathode, and an organic luminescence medium between these electrodes.

An organic luminescence medium is formed of a multi-layer stack of layers having their respective functions. For example, an organic luminescence medium is a multilayer stack in which an anode, a hole-injecting layer, a hole-transporting layer, an emitting layer, an electron-transporting layer and an electron-injecting layer are sequentially stacked.

As the emitting material of the emitting layer, a material which emits each color (red, green and blue, for example) has been developed. For example, use of a pyrene derivative is disclosed in Patent Documents 1 to 3.

However, further improvement of luminous efficiency is required.

RELATED ART DOCUMENTS

Patent Documents

Patent Document 1: JP-A-2003-234190
Patent Document 2: JP-A-2005-126431
Patent Document 3: JP-A-2009-4351

SUMMARY OF THE INVENTION

The invention is aimed at providing a compound capable of producing an organic electroluminescence device having a high luminous efficiency.

According to the invention, the following pyrene derivative or the like are provided.
1. A pyrene derivative represented by the following formula (1);

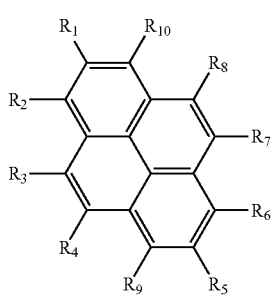

wherein $R_1$ to $R_{10}$ are independently a hydrogen atom, a substituted or unsubstituted aryl group, a substituted or unsubstituted alkyl group, a substituted or unsubstituted cycloalkyl group or a group represented by the following formula (2), at least one of $R_1$ to $R_{10}$ is a group represented by the formula (2) and at least two of $R_1$ to $R_{10}$ are a substituted or unsubstituted aryl group, provided that in the case where only one of $R_1$ to $R_{10}$ is a group represented by the formula (2), at least one of the substituted or unsubstituted aryl groups is an aryl group having 10 to 50 carbon atoms;

wherein X, Y and Z are independently a substituted or unsubstituted alkyl group, a substituted or unsubstituted aryl group or a substituted or unsubstituted alkoxy group.
2. The pyrene derivative according to 1 wherein $R_9$ and $R_{10}$ are a substituted or unsubstituted aryl group.
3. The pyrene derivative according to 2 wherein $R_2$ or $R_6$ is a group represented by the formula (2).
4. The pyrene derivative according to 3 wherein one of $R_2$ and $R_6$ is a group represented by the formula (2), the other is a substituted or unsubstituted aryl group or a substituted or unsubstituted alkyl group, and $R_1$, $R_3$ to $R_5$, $R_7$ and $R_8$ are a hydrogen atom.
5. The pyrene derivative according to 2 wherein $R_2$ and $R_6$ are a group represented by the formula (2).
6. The pyrene derivative according to 2 wherein $R_1$ to $R_8$ are independently a hydrogen atom or a group represented by the formula (2).
7. An organic electroluminescence device comprising a pair of electrodes and an organic luminescent medium therebetween, the organic luminescent medium comprising one or more organic compound layers comprising an emitting layer, wherein the organic luminescent medium comprises at least one of the pyrene derivative according to any of 1 to 6.
8. The organic electroluminescence device according to 7, wherein the emitting layer comprises the pyrene derivative.
9. The organic electroluminescence device according to 8, wherein the content of the pyrene derivative in the emitting layer is 0.01 to 20 mass %.

According to the invention, it is possible to provide a compound capable of producing an organic electroluminescence device having a high luminous efficiency.

BEST MODE FOR CARRYING OUT THE INVENTION

The pyrene derivative of the invention is represented by the following formula (1);

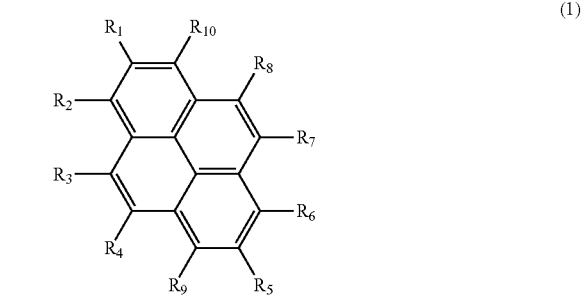

In formula (1), $R_1$ to $R_{10}$ are independently a hydrogen atom, a substituted or unsubstituted aryl group, a substituted or unsubstituted alkyl group, a substituted or unsubstituted cycloalkyl group or a group represented by the following formula (2). At least one of $R_1$ to $R_{10}$ is a group represented by the formula (2) and at least two of $R_1$ to $R_{10}$ are a substituted or unsubstituted aryl group.

In this regard, in the case where only one of $R_1$ to $R_{10}$ is a group represented by the formula (2), at least one of the substituted or unsubstituted aryl groups is an aryl group having 10 to 50 carbon atoms;

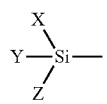

(2)

In formula (2), X, Y and Z are independently a substituted or unsubstituted alkyl group, a substituted or unsubstituted aryl group or a substituted or unsubstituted alkoxy group.

Although a pyrene skeleton is the center of emission, association is likely to occur due to its high planarity. The pyrene derivative of the invention has two or more substituted or unsubstituted aryl groups and has a group represented by the following formula (2) directly on the pyrene skeleton, and thus it is believed that luminous efficiency is increased using the pyrene derivative since association in a part where association is most likely to occur is controlled.

Hereinbelow, each substituent of the pyrene derivative of the invention will be explained.

In the invention, the "aryl group" means a "group which is obtained by removing a hydrogen atom from an aromatic compound", and includes not only a monovalent aryl group but also an "arylene group" which is a divalent group.

The hydrogen atom of the compound of the invention includes light hydrogen and heavy hydrogen.

The substituted or unsubstituted aryl group represented by $R_1$ to $R_{10}$ is preferably a substituted or unsubstituted aryl group having 6 to 50 carbon atoms that form a ring (hereinafter referred to as "ring carbon atoms"). Examples thereof include a substituted or unsubstituted phenyl group, a substituted or unsubstituted naphthyl group, a substituted or unsubstituted fluorenyl group, a substituted or unsubstituted phenanthryl group, a substituted or unsubstituted anthracenyl group, a substituted or unsubstituted biphenyl group, and a substituted or unsubstituted terphenyl group.

A substituted or unsubstituted aryl group having 6 to 20 ring carbon atoms is preferable. Examples thereof include a substituted or unsubstituted phenyl group, a substituted or unsubstituted naphthyl group, a substituted or unsubstituted fluorenyl group, a substituted or unsubstituted phenanthryl group and a substituted or unsubstituted biphenyl group.

In particular, a phenyl group substituted by an alkyl group, an aryl group or an alkylsilyl group and an unsubstituted phenyl group are preferable. Examples thereof include a 4-trimethylsilylphenyl group, a 3-methylphenyl group, a 4-methylphenyl group, a 3-naphthylphenyl group and a 4-naphthylphenyl group.

A naphthyl group substituted by an alkyl group, an aryl group or an alkylsilyl group and an unsubstituted naphthyl group are preferable. Examples thereof include a 1-naphthyl group, a 2-naphthyl group and a naphthyl group substituted by a phenyl group (particularly 6-phenyl-2-naphthyl group).

A phenanthryl group substituted by an alkyl group, an aryl group or an alkylsilyl group and an unsubstituted phenanthryl group are preferable. Examples thereof include a 2-phenanthryl group, a 3-phenanthryl group and a 9-phenanthryl group.

A fluorenyl group substituted by an alkyl group, an aryl group or an alkylsilyl group and an unsubstituted fluorenyl group are preferable. Examples thereof include a fluorenyl group, a 9,9-dimethylfluorenyl group, a diethylfluorenyl group, a dipropylfluorenyl group, a diisopropylfluorenyl group, a dibutylfluorenyl group, a diphenylfluorenyl group, and a benzofluorenyl group.

In addition, a biphenyl group substituted by an alkyl group, an aryl group or an alkylsilyl group and an unsubstituted biphenyl group are preferable. In particular, a 4-biphenyl group is preferable.

As the substituent which may further substitute the above aryl group, for example, a fluorine atom, a substituted silyl group, a cyano group, a substituted or unsubstituted aryl group, a substituted or unsubstituted alkyl group, a substituted or unsubstituted cycloalkyl group and the like are given, and a substituted silyl group, a substituted or unsubstituted aryl group, a substituted or unsubstituted alkyl group and a substituted or unsubstituted cycloalkyl group are preferable.

Examples of these groups are the same as the above-mentioned or later mentioned substituents.

In addition, in the case where $R_1$ to $R_{10}$, X, Y and Z further have a substituent, the substituent is the same as above (for example, the substituent includes a substituent which bonds to the substituted or unsubstituted aryl group having 6 to 50 ring carbon atoms. this applies to all the substituent in the expression "substituted or unsubstituted").

As substituted or unsubstituted alkyl group, a substituted or unsubstituted alkyl group having 1 to 20 carbon atoms is given and the examples thereof include a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted s-butyl group, a substituted or unsubstituted isobutyl group, a substituted or unsubstituted t-butyl group, a substituted or unsubstituted n-pentyl group, a substituted or unsubstituted n-hexyl group, a substituted or unsubstituted n-heptyl group and a substituted or unsubstituted octyl group. The alkyl group is preferably a substituted or unsubstituted alkyl group having 1 to 5 carbon atoms and the examples thereof include a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted s-butyl group, a substituted or unsubstituted isobutyl group and a substituted or unsubstituted t-butyl group, with a substituted or unsubstituted methyl group, a substituted or unsubstituted ethyl group, a substituted or unsubstituted propyl group, a substituted or unsubstituted isopropyl group, and a substituted or unsubstituted t-butyl group being particularly preferable. The alkyl group is preferably a substituted or unsubstituted alkyl group having 1 to 10 carbon atoms, and more preferably a substituted or unsubstituted alkyl group having 1 to 6 carbon atoms.

As the substituted or unsubstituted cycloalkyl group, a substituted or unsubstituted cycloalkyl group having 3 to 15 carbon atoms is given, and the examples thereof include a substituted or unsubstituted cyclopropyl group, a substituted or unsubstituted cyclobutyl group, a substituted or unsubstituted cyclopentyl group, a substituted or unsubstituted cyclohexyl group, a substituted or unsubstituted 4-methylcyclohexyl group, a substituted or unsubstituted 1-adamantyl group, a substituted or unsubstituted 2-adamantyl group, a substituted or unsubstituted 1-norbonyl group and a substituted or unsubstituted 2-norbonyl group. A substituted or unsubstituted cycloalkyl group having 5 to 7 carbon atoms is preferable and the examples thereof include a substituted or unsubstituted cyclopentyl group and a substituted or unsubstituted cyclohexyl group.

As the substituted or unsubstituted alkyl group and substituted or unsubstituted aryl group represented by X, Y and Z in the formula (2), the same groups as $R_1$ to $R_{10}$ are given.

The substituted or unsubstituted alkoxy group represented by X, Y and Z of the formula (2) is represented by —OY' and examples of Y' include the examples of the above-mentioned alkyl group.

Specific examples of the substituted silyl group and the group represented by the formula (2) include a trimethylsilyl group, a triethylsilyl group, a t-butyldimethylsilyl group, a vinyldimethylsilyl group, a propyldimethylsilyl group, a triphenylsilyl group and a triisopropylsilyl group. The substituted silyl group and formula (2) is preferably a trimethylsilyl group, a triethylsilyl group and a t-butyldimethylsilyl group.

In the pyrene derivative of the invention, it is preferable that $R_9$ and $R_{10}$ in the formula (1) be a substituted or unsubstituted aryl group.

In addition, in the pyrene derivative of the invention, it is preferable that $R_2$ or $R_6$ of the formula (1) be a group represented by the formula (2).

In this case, a pyrene derivative in which one of $R_2$ and $R_6$ is a group represented by the formula (2), the other is a substituted or unsubstituted aryl group or a substituted or unsubstituted alkyl group, and $R_1$, $R_3$ to $R_5$, $R_7$ and $R_8$ are a hydrogen atom is preferable.

A pyrene derivative in which $R_2$ and $R_6$ of the formula (1) are a group represented by the formula (2) is preferable.

Further, a pyrene derivative in which $R_1$ to $R_8$ are independently a hydrogen atom or a group represented by the formula (2) is preferable.

In the pyrene derivative represented by the formula (1), pyrene derivatives represented by the following formulas (3) to (8) are preferable:

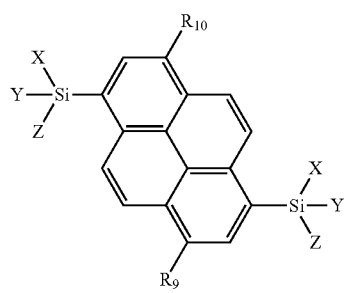

(3)

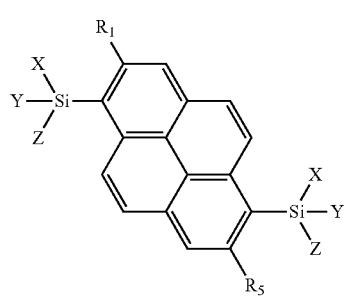

(4)

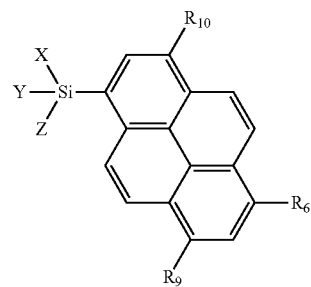

(5)

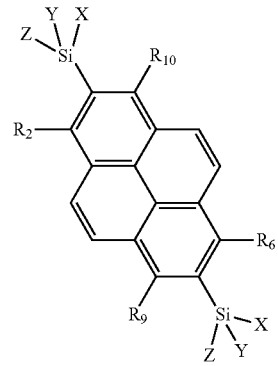

(6)

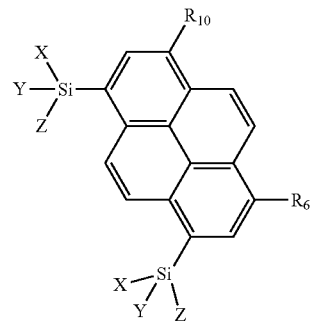

(7)

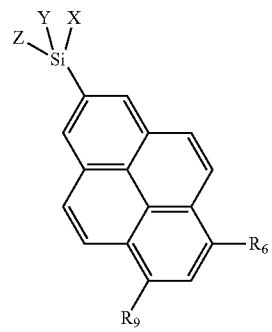

(8)

wherein $R_1$, $R_2$, $R_5$, $R_6$, $R_9$ and $R_{10}$ are the same as mentioned above.

Specific examples of the pyrene derivative of the invention are shown below.

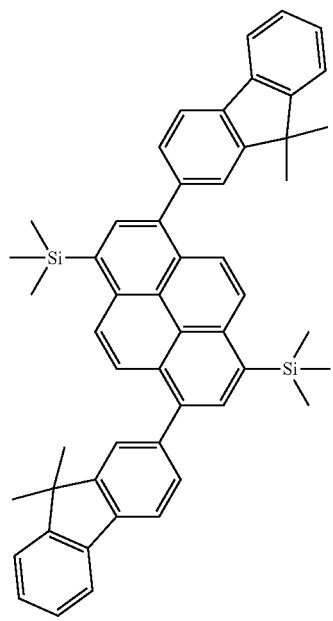
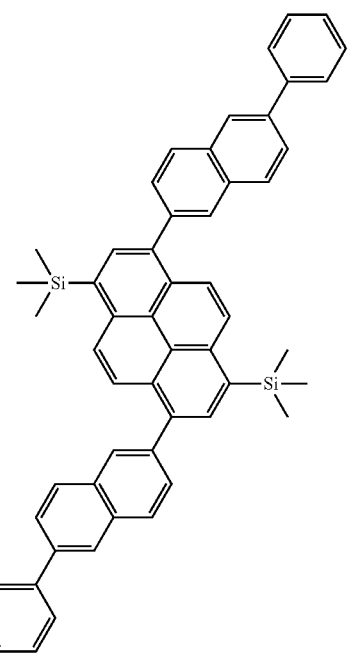
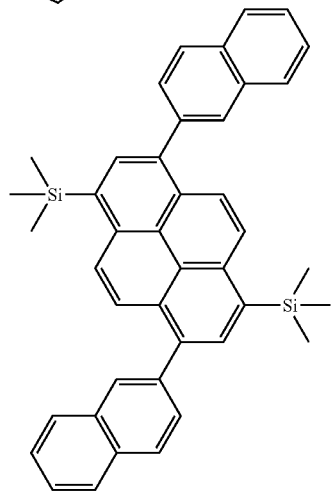
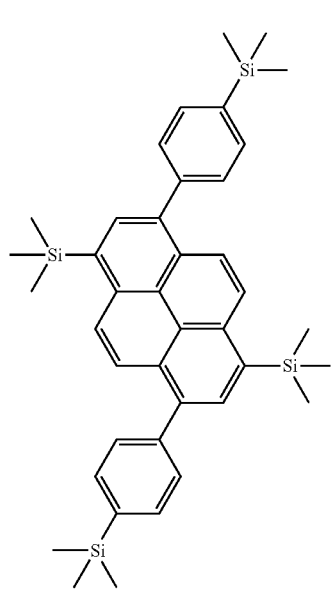
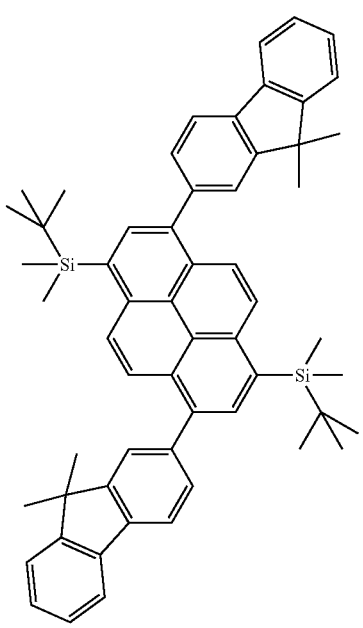

-continued
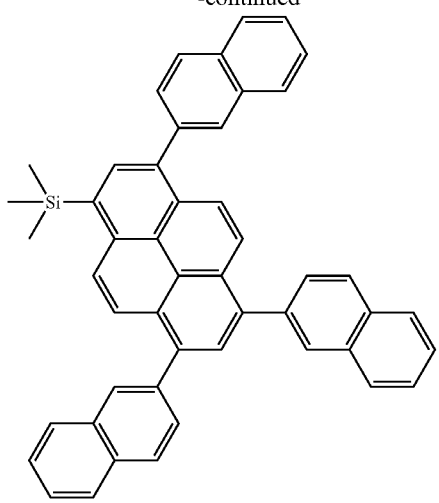
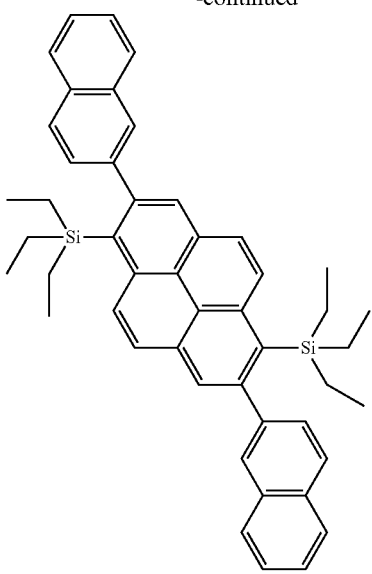
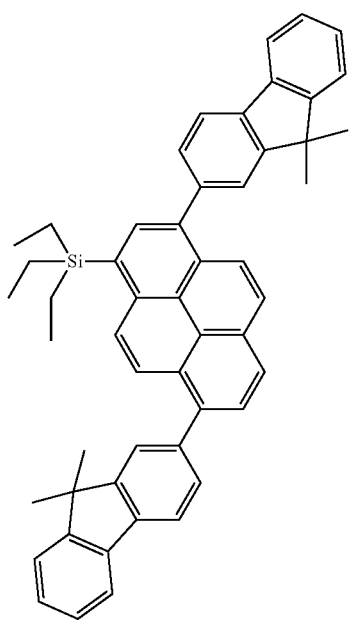
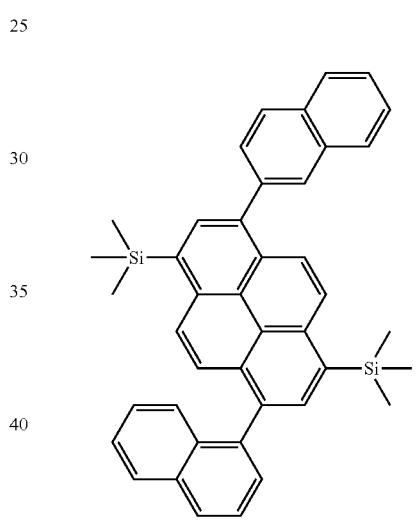
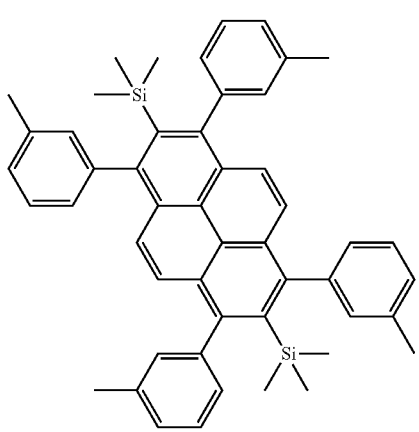
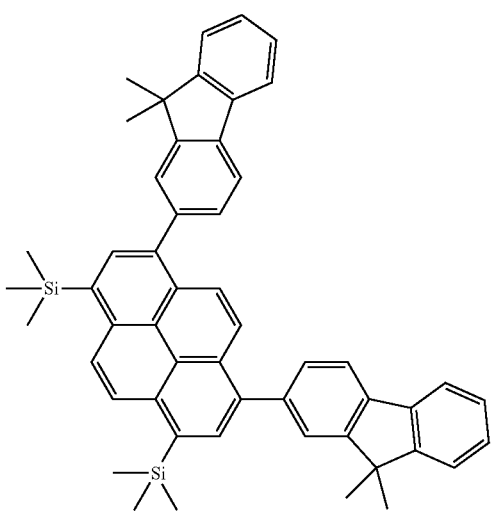

-continued
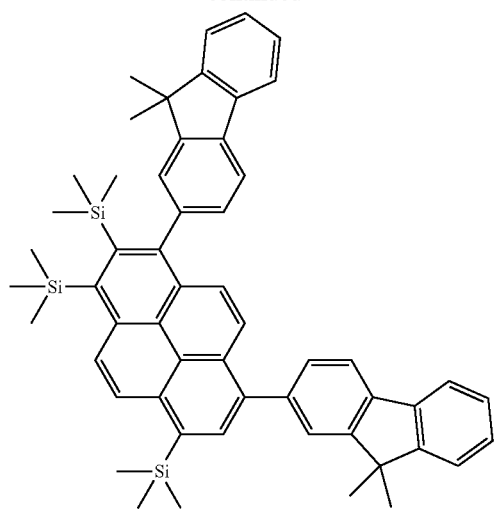
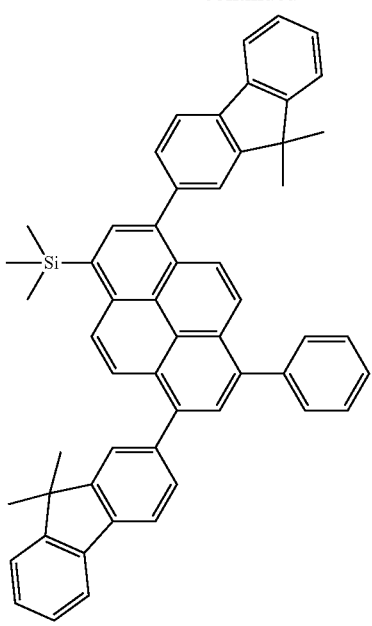
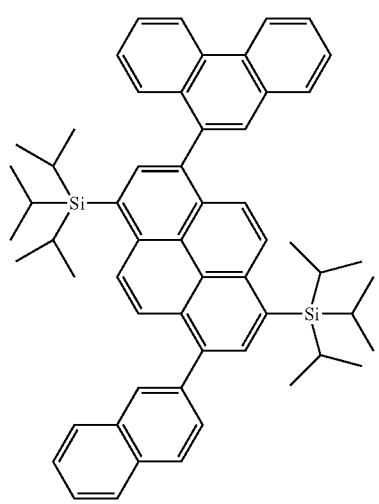
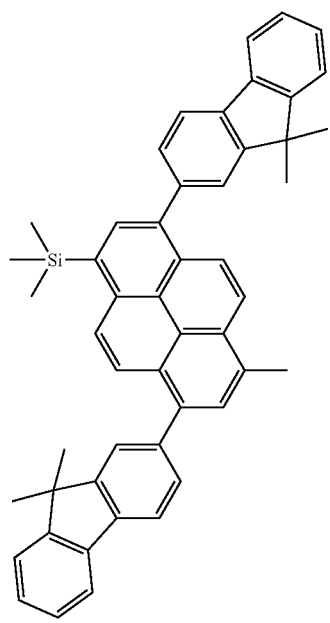
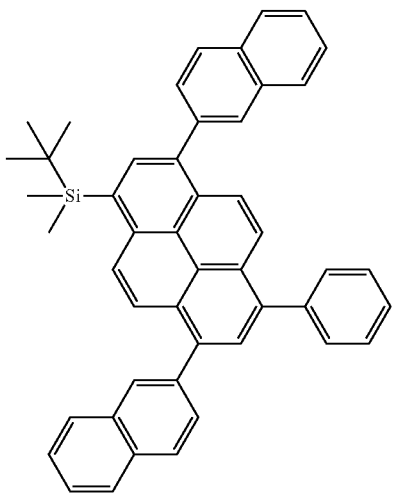

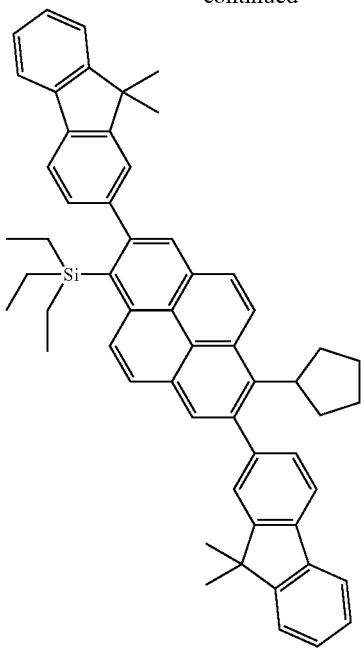
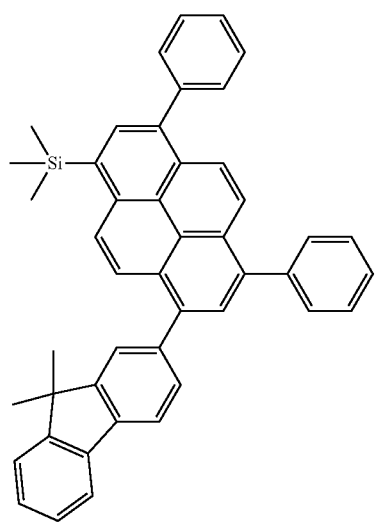
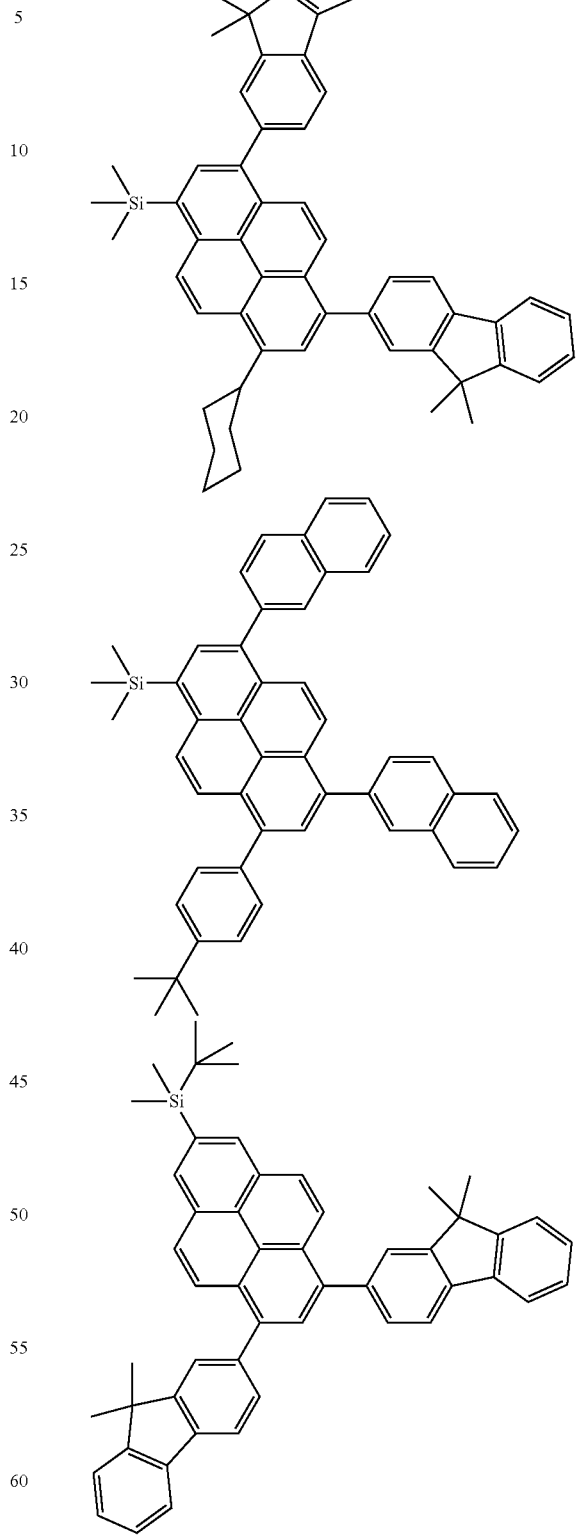
The pyrene derivative of the invention can be obtained by a Suzuki coupling reaction or the like by using as starting materials a halogenated pyrene compound and an arylboronic acid compound, or a halogenated aryl compound and a pyrenylboronic acid compound, which are synthesized by a known method. The pyrene derivative of the invention can be obtained by subjecting the thus obtained precursor to a halogenation reaction, a boronation reaction and a Suzuki coupling reaction in an appropriately combined manner.

In addition, for example, the pyrene derivative can be obtained by lithiating a halogenated pyrenyl compound and reacting with a silylation agent such as trimethylsilylchloride.

Many reports have been made on the above-mentioned Suzuki coupling reaction (Chem. Rev., Vol. 95, No. 7, 2457 (1995)). The reaction can be conducted under the reported conditions.

No specific restrictions are made on the halogenation agent used in the above-mentioned halogenation reaction. However, N-halogenated succinimide is preferably used. The amount of the halogenation agent is normally 0.8 to 10 molar equivalents, preferably 1 to 5 molar equivalents, relative to the base.

The boronation reaction can be conducted by a known method (pages 61 to 90 of vol. 24 of the Fourth Series of Experimental Chemistry edited by the Chemical Society of Japan or J. Org. Chem., Vol. 60, 7508 (1995) or the like).

The pyrene derivative of the invention is preferably used as a material for an organic EL device. In particular, it is further preferred that the pyrene derivative of the invention be used as a doping material of an organic EL device.

Regarding the organic EL device of the invention, in the organic EL device in which one or a plurality of organic compound layers including an emitting layer are held between a pair of electrodes, the emitting layer comprises the pyrene derivative of the invention.

In the organic EL device of the invention, the emitting layer preferably comprises the pyrene derivative of the invention, the pyrene derivative of the invention is contained preferably in an amount of 0.01 to 20 mass %, further preferably 0.5 to 20 mass %, particularly preferably 1 to 18 mass %, and most preferably 2.5 to 15 mass %.

The organic EL device using a material for an organic EL device containing the pyrene derivative of the invention can emit blue light.

If the pyrene derivative of the invention is used as the emitting material of an organic EL device, it is preferred that the emitting layer contain at least one of the pyrene derivative represented by the formula (1) and at least one selected from the anthracene derivative represented by the following formula (10) or the pyrene derivative represented by the formula (11). It is preferred that the derivative represented by the following formula (10) or (11) be a host material.

The anthracene derivative represented by the formula (10) is the following compound.

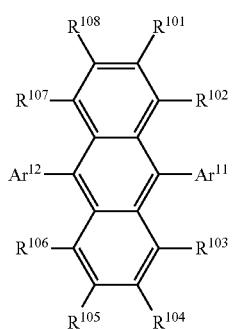

(10)

In the formula (10), $Ar^{11}$ and $Ar^{12}$ are independently a substituted or unsubstituted monocyclic group having 5 to 50 atoms that form a ring (hereinafter referred to as "ring atoms"), a substituted or unsubstituted fused cyclic group having 8 to 50 ring atoms or a group formed of a combination of a monocyclic group and a fused cyclic group; $R^{101}$ to $R^{108}$ are independently an atom or a group selected from a hydrogen atom, a substituted or unsubstituted monocyclic group having 5 to 50 ring atoms, a substituted or unsubstituted fused cyclic group having 8 to 50 ring atoms, a group formed of a monocyclic group and a fused cyclic group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom and a cyano group.

In the formula (10), the monocytic group is a group formed only of a ring structure having no fused structure.

Specific preferable examples of the monocyclic group having 5 to 50 ring atoms (preferably 5 to 30 ring atoms, more preferably 5 to 20 ring atoms) include aromatic groups such as a phenyl group, a biphenyl group, a terphenyl group and a quarterphenyl group and heterocyclic groups such as a pyridyl group, a pyrazyl group, a pyrimidyl group, a triazinyl group, a furyl group and a thienyl group.

Of these, a phenyl group, a biphenyl group and a terphenyl group are preferable.

In the formula (10), the fused cyclic group is a group formed by fusing two or more ring structures.

Specifically, as examples of the fused cyclic group having 8 to 50 ring atoms (preferably, 8 to 30 ring atoms, more preferably 8 to 20 ring atoms), a fused aromatic group such as a naphthyl group, a phenanthryl group, an anthryl group, a chrysenyl group, a benzanthryl group, a benzophenanthryl group, a triphenylenyl group, a benzochryceny group, an indenyl group, a fluorenyl group, 9,9-dimethylfluorenyl group, a benzofluorenyl group, a dibenzofluorenyl group, a fluoranthenyl group and a benzofluoranthenyl group or a fused heterocyclic group such as a benzofuranyl group, a benzothiophenyl group, an indolyl group, a dibenzofuranyl group, a dibenzothiophenyl group, a carbazolyl group, a quinolyl group and a phenanthrolinyl group are preferable.

Of these, a naphthyl group, a phenanthryl group, an anthryl group, a 9,9-dimethylfluorenyl group, a fluoranthenyl group, a benzanthryl group, a dibenzothiophenyl group, a dibenzofuranyl group and a carbazolyl group are preferable.

The specific examples of the alkyl group, the substituted silyl group, the cyclcoalkyl group and the alkoxy group in the formula (10) are the same as the specific examples of each group represented by $R_1$ to $R_{10}$, X, Y and Z in the formula (1) and the substituent in the "further substituent of each of the substituents".

The aryloxy group is represented by —OZ. Examples of Z include the examples of the above-mentioned aryl group or the examples of the monocyclic group and the fused cyclic group which will be mentioned later. The aryloxy group is a phenoxy group, for example.

The aralkyl group is represented by —Y—Z, and examples of Y include alkylene groups corresponding to the examples of the alkyl group, and examples of Z are the same as those of the aryl group. The aralkyl group is an aralkyl group having 7 to 50 carbon atoms (the aryl part has 6 to 49 (preferably 6 to 30, more preferably 6 to 20, and particularly preferably 6 to 12) carbon atoms, the alkyl part has 1 to 44 (preferably 1 to 30, more preferably 1 to 20, further preferably 1 to 10 and particularly preferably 1 to 6) carbon atoms). The aralkyl group is a benzyl group, a phenylethyl group or a 2-phenylpropane-2-yl group, for example.

As the halogen atom, fluorine, chlorine, bromine and iodine and the like are given, and fluorine atom is preferable.

As the substituents of the "substituted or unsubstituted" groups represented by $Ar^{11}$, $Ar^{12}$ and $R^{101}$ to $R^{108}$, a monocyclic group, a fused cyclic group, an alkyl group, a cycloalkyl group, a substituted silyl group, an alkoxy group, a cyano group and a halogen atom (fluorine, in particular) are preferable. A monocyclic group and a fused cyclic group are particularly preferable. Specific examples of preferable substituents are the same as the groups in the formula (10) and the groups in the formula (1).

It is preferred that the anthracene derivative represented by the formula (10) be any of the following anthracene derivatives (A), (B) and (C). A preferable anthracene derivative represented by the formula (10) is selected according to the constitution or required properties of an organic EL device to which the anthracene derivative is applied.

(Anthracene Derivative (A))

In this anthracene derivative, $Ar^{11}$ and $Ar^{12}$ in the formula (10) are independently a substituted or unsubstituted fused cyclic group having 8 to 50 ring atoms. This anthracene derivative can be divided into a derivative in which $Ar^{11}$ and $Ar^{12}$ are the same substituted or unsubstituted fused cyclic group and a derivative in which $Ar^{11}$ and $Ar^{12}$ are the different substituted or unsubstituted fused cyclic groups.

An anthracene derivative in which $Ar^{11}$ and $Ar^{12}$ in the formula (10) are different (including the difference in substitution position) substituted or unsubstituted fused cyclic group is particularly preferable. Specific preferable examples of the fused cyclic group are as mentioned above. Of these, a naphthyl group, a phenanthryl group, a benzanthryl group, a 9,9-dimethylfluorenyl group and a dibenzofuranyl group are preferable.

(Anthracene Derivative (B))

In this anthracene derivative, one of $Ar^{11}$ and $Ar^{12}$ in the formula (10) is a substituted or unsubstituted fused monocyclic group having 5 to 50 ring atoms and the other is a substituted or unsubstituted fused cyclic group having 8 to 50 ring atoms.

In a preferred mode, $Ar^{12}$ is a naphthyl group, a phenanthryl group, a benzanthryl group, a 9,9-dimethylfluorenyl group or a dibenzofuranyl group, and $Ar^{11}$ is a phenyl group which is substituted by a monocyclic group or a fused cyclic group.

Specific examples of a preferable monocyclic group and a fused cyclic group are as mentioned above.

In another preferable mode, $Ar^{12}$ is a fused cyclic group and $Ar^{11}$ is an unsubstituted phenyl group. In this case, as the fused cyclic group, a phenanthryl group, a 9,9-dimethylfluorenyl group, a dibenzofuranyl group and a benzoanthryl group are particularly preferable.

(Anthracene Derivative (C))

In this anthracene derivative, $Ar^{11}$ and $Ar^{12}$ in the formula (10) are independently a substituted or unsubstituted monocyclic group having 5 to 50 ring atoms.

In a preferred mode, $Ar^{11}$ and $Ar^{12}$ are both a substituted or unsubstituted phenyl group.

In a further preferred mode, the anthracene derivative (C) is divided into a derivative in which $Ar^{11}$ is an unsubstituted phenyl group and $Ar^{12}$ is a phenyl group having a monocyclic group or a fused cyclic group as a substituent and a derivative in which $Ar^{11}$ and $Ar^{12}$ are independently a phenyl group having a monocyclic group or a fused cyclic group.

Specific examples of the monocyclic group or the fused cyclic group which is preferable as the substituent are as mentioned above. As the monocyclic group as the substituent, a phenyl group and a biphenyl group are further preferable, and as the fused cyclic group as the substituent, a naphthyl group, a phenanthryl group, a 9,9-dimethylfluoronenyl group, a dibenzofuranyl group and a benzanthryl group are preferable.

The pyrene derivative represented by the formula (11) is the following compound.

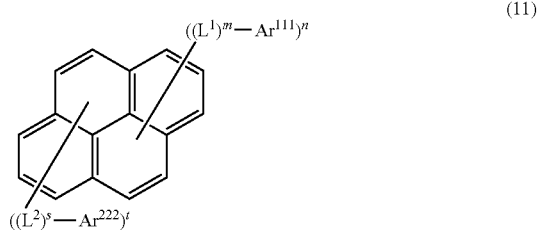

(11)

In the formula (11), $Ar^{111}$ and $Ar^{222}$ are independently a substituted or unsubstituted aryl group having 6 to 30 ring carbon atoms.

$L^1$ and $L^2$ are independently a substituted or unsubstituted divalent aryl group having 6 to 30 ring carbon atoms or a heterocyclic group.

m is an integer of 0 to 1, n is an integer of 1 to 4, s is an integer of 0 to 1 and t is an integer of 0 to 3.

$L^1$ or $Ar^{111}$ bonds to any of the $1^{st}$ to $5^{th}$ positions of the pyrene, and $L^2$ or $Ar^{222}$ bonds to any of the $6^{th}$ to $10^{th}$ positions of the pyrene.

$L^1$ and $L^2$ in the general formula (11) is preferably a divalent aryl group formed of a substituted or unsubstituted phenylene group, a substituted or unsubstituted biphenylene group, a substituted or unsubstituted naphthylene group, a substituted or unsubstituted terphenylene group, a substituted or unsubstituted fluorenylene group or a combination of these substituents.

As the substituent, the same substituents as those given in the "further substituent of each of the substituents" in the above-mentioned formula (1) can be given. The substituents of $L^1$ and $L^2$ are preferably an alkyl group having 1 to 20 carbon atoms.

m in the general formula (11) is preferably an integer of 0 to 1. n in the general formula (11) is preferably an integer of 1 to 2. s in the general formula (11) is preferably an integer of 0 to 1.

t in the general formula (11) is preferably an integer of 0 to 2.

The aryl groups of $Ar^{111}$ and $Ar^{222}$ are the same as those in the above-mentioned formula (1).

The aryl groups of $Ar^{111}$ and $Ar^{222}$ are preferably a substituted or unsubstituted aryl group having 6 to 20 ring carbon atoms, more preferably a substituted or unsubstituted aryl group having 6 to 16 ring carbon atoms. Specific examples of the aryl group include an phenyl group, a naphthyl group, a phenanthryl group, a fluorenyl group, a biphenyl group, an anthryl group and a pyrenyl group.

In the organic EL device of the invention, each organic layer such as an emitting layer can be formed by a dry film-forming method such as vacuum vapor deposition, molecular beam epitaxy (MBE), sputtering, plasma ion coating, ion plating or the like or a coating method such as spin coating, dipping, casting, bar coating, roll coating, flow coating, ink jetting or the like of a solution obtained by dissolving in a solvent.

In particular, when an organic EL device is produced by using the pyrene derivative of the invention, an organic compound layer and an emitting layer can be formed not only by deposition but also by a wet method.

Although the film thickness of each of the organic compound layers is not particularly limited, it is required to adjust the film thickness to an appropriate value. If the film thickness is too small, pinholes or the like are generated, and a sufficient luminance cannot be obtained even if an electrical field is applied. If the film thickness is too large, a large voltage is required to be applied in order to obtain a certain optical output, which results in a poor efficiency. The suitable film thickness is normally 5 nm to 10 µm, with a range of 10 nm to 0.2 µm being further preferable.

The pyrene derivative of the invention and the anthracene derivative (10) or the pyrene derivative (11) mentioned above can be used in the hole-injecting layer, the hole-transporting layer, the electron-injecting layer and the electron-transporting layer in addition to the emitting layer.

In the invention, as the organic EL device in which the organic compound layer (organic thin film layer) is composed of plural layers, one in which layers are sequentially stacked (anode/hole-injecting layer/emitting layer/cathode), (anode/emitting layer/electron-injecting layer/cathode), (anode/hole-injecting layer/emitting layer/electron-injecting layer/cathode), (anode/hole-injecting layer/hole-transporting layer/emitting layer/electron-injecting layer/cathode) or the like can be given.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such a case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the material other than the derivative represented by the formula (10) or (11) which can be used in the emitting layer together with the pyrene derivative of the invention include, though not limited thereto, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene and spirofluorene and derivatives thereof, organic metal complexes such as tris(8-quinolinolate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acrylidone derivatives and quinacridone derivatives.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeletons.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imidazopyridine derivative are preferable.

As a preferred mode, a dopant is further contained in these electron-injecting materials. In order to facilitate receiving electrons from the cathode, it is more preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one selected from the pyrene derivatives represented by the formulas (1), at least one of an emitting material, doping material, hole-injecting material, hole-transporting material and electron-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma ion coating, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solvent suited to such a wet film-forming method, a solution containing the pyrene derivative of the invention as an organic EL material and a solvent can be used.

It is preferred that the organic EL material contain a host material and a dopant material, that the dopant material be the pyrene derivative of the invention, and that the host material be at least one selected from the compounds represented by the formula (10).

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, navigation light, or the like. The compound of the invention can be used not only in an organic EL device but also in the field of an electrophotographic photoreceptor, a photoelectric converting element, a solar cell and an image sensor.

EXAMPLES

Example 1

Pyrene derivative (D-1) shown below was synthesized:

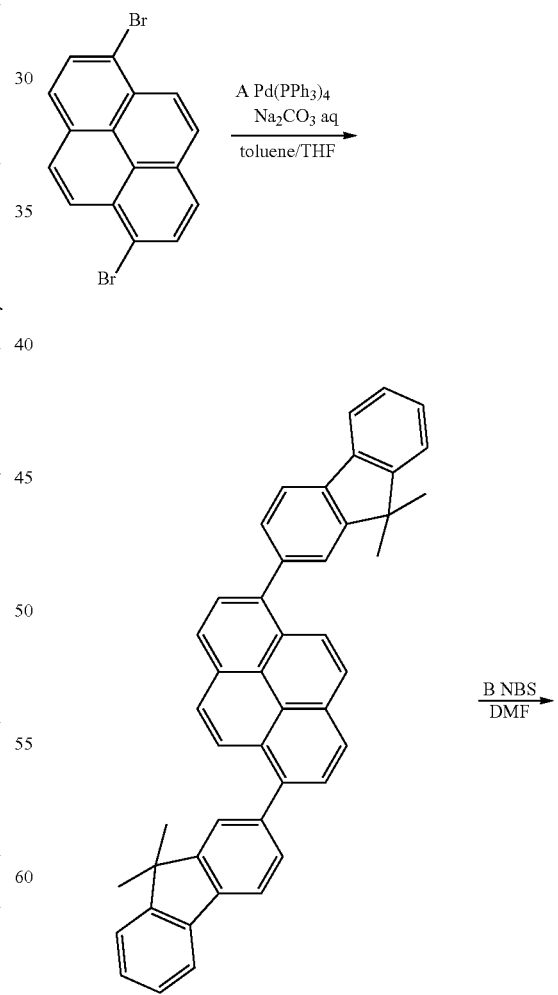

Intermediate a

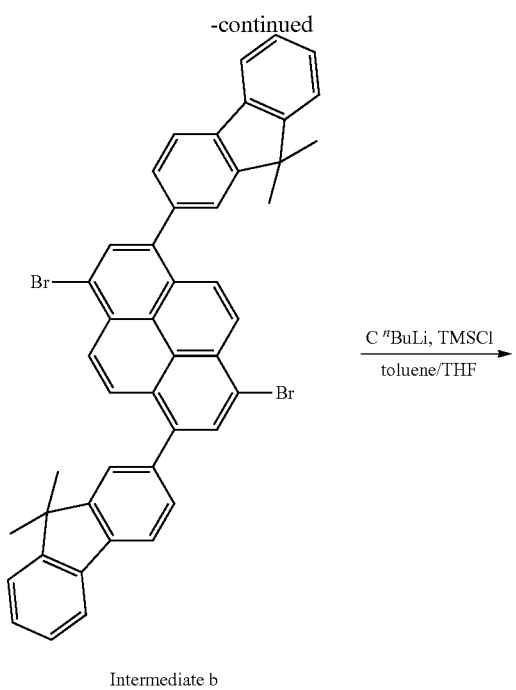

Intermediate b

D-1

(1) Synthesis of Intermediate a

Under a flow of argon, in a 1000 mL-recovery flask, 15.0 g (41.6 mmol) of 1,6-dibromopyrene, 25.8 g (108 mmol) of 9,9-dimethylfluorene-2-ylboronic acid, 1.9 g (1.67 mmol) of tetrakis(triphenylphosphine)palladium (0) [Pd(PPh$_3$)$_4$], 27.8 g (262 mmol) of sodium carbonate (130 mL of clean water), toluene and tetrahydrofuran were placed, and the resulting mixture was allowed to react at 90° C. for 7 hours. After cooling, the reaction solution was filtered, and solids obtained were washed with methanol and clean water. Further, the solids were purified by silica gel chromatography (heated toluene) and concentrated. The resulting crude product was re-crystallized from toluene, followed by drying under a reduced pressure, whereby 24.0 g of white solids were obtained.

As a result of a FD-MS (Field desorption mass spectrometry) analysis, the resulting white solids were identified as intermediate a.

(2) Synthesis of Intermediate b

Under a flow of argon, in a 2000 mL-recovery flask, 19.6 g (33.4 mmol) of intermediate a, 14.9 g (83.5 mmol) of N-bromosuccinimide and dimethylformamide were placed. The resulting mixture was allowed to react at 50° C. for 5 hours. After cooling, the reaction solution was filtered, and solids obtained were washed with clean water, methanol and ethyl acetate, and solids obtained were dried under a reduced pressure, whereby 20.1 g of yellow white solids were obtained.

As a result of a FD-MS analysis, the resulting solids were identified as intermediate b.

(3) Synthesis of D-1

Under a flow of argon, in a 1000 mL-recovery flask, 20.1 g (27.1 mmol) of intermediate b, toluene and tetrahydrofuran were placed, the resulting mixture was cooled to –70° C., and 65.6 mL (108 mmol) of n-butyllithium (1.65M hexane solution) was added. The resulting mixture was stirred for 10 minutes, then heated to 0° C., and stirred for 90 minutes. Thereafter, the resulting mixture was cooled to –70° C., and 13.7 mL (108 mmol) of trimethylsilylchloride was added. The resulting mixture was heated to 0° C., stirred for 2 hours, and then heated to room temperature, followed by stirring for 1 hour.

The reaction solution was filtered, solids obtained were dissolved in toluene and clean water was added. After separation and extraction, the extracted matter was washed with clean water and saturated saline and dried with sodium sulfate, followed by concentration. Crystals obtained were re-crystallized from toluene twice, followed by drying under a reduced pressure, whereby 3.5 g of yellow white solids were obtained. As for the compound obtained, FDMS, a UV absorption maximum wavelength in the toluene solution λmax and a fluorescent emission maximum wavelength were shown below.

FDMS, calcd for C$_{52}$H$_{50}$Si$_2$=730. found m/z=730 (M+).

UV (PhMe); λmax, 397 nm, FL (PhMe, λex=370 nm); λmax, 438 nm

Example 2

Pyrene derivative (D-2) shown below was synthesized:

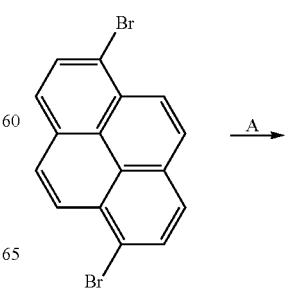

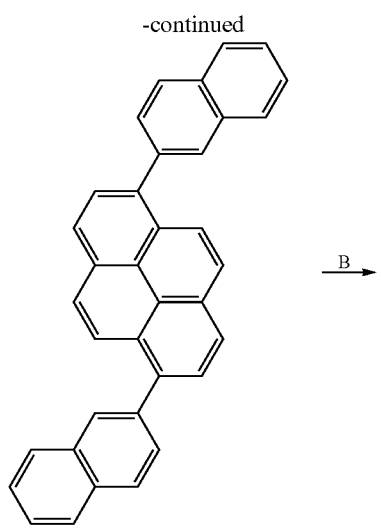

Intermediate c

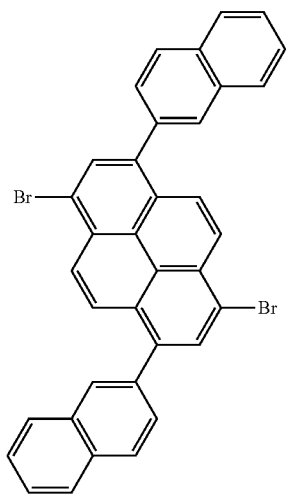

Intermediate d

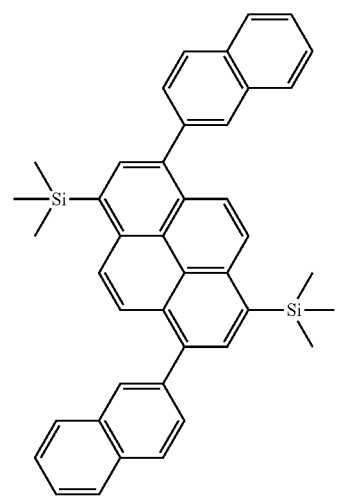

D-2

(1) Synthesis of Intermediate c

Intermediate c was synthesized by conducting a reaction in the same manner as in the synthesis of intermediate a, except that 2-naphthaleneboronic acid was used instead of 9,9-dimethylfluorene-2-ylboronic acid. Intermediate c was identified by a FD-MS analysis.

(2) Synthesis of Intermediate d

Intermediate d was synthesized by conducting a reaction in the same manner as in the synthesis of intermediate b, except that intermediate c was used instead of intermediate a. Intermediate d was identified by a FD-MS analysis.

(3) Synthesis of D-2

D-2 was synthesized by conducting a reaction in the same manner as in the synthesis of D-1, except that intermediate d was used instead of intermediate b. As for the compound obtained, FDMS, a UV absorption maximum wavelength in the toluene solution λmax and a fluorescent emission maximum wavelength were shown below.

FDMS, calcd for $C_{42}H_{38}Si_2$=598. found m/z=598 (M+).

UV (PhMe); λmax, 394 nm, FL (PhMe, λex=360 nm); λmax, 427 nm

Example 3

Pyrene derivative (D-3) shown below was synthesized:

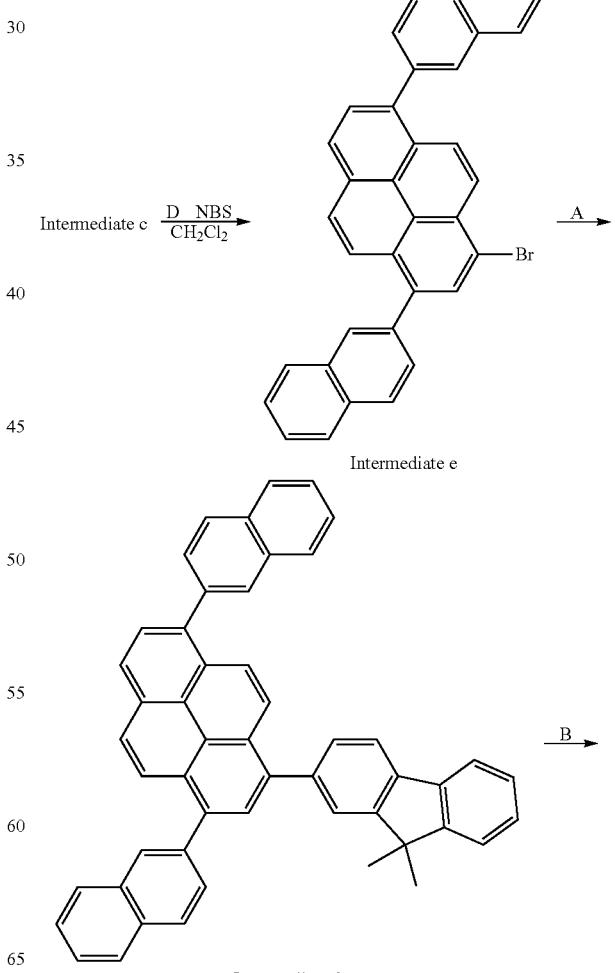

Intermediate e

Intermediate f

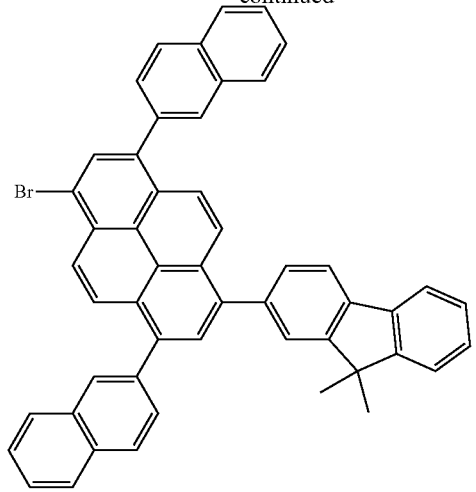

Intermediate g

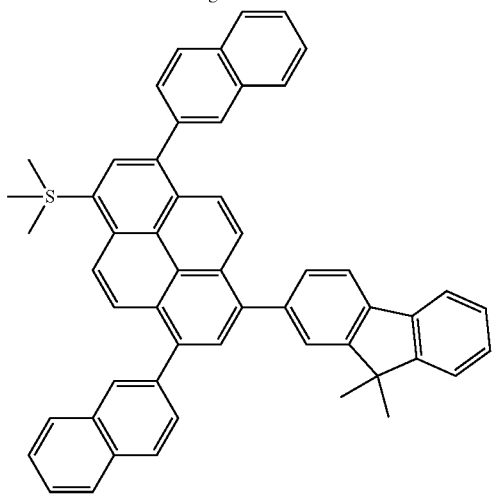

D-3

(1) Synthesis of Intermediate e

Under a flow of argon, in a 2000 mL-recovery flask, 4.0 g (8.8 mmol) of intermediate c, 1.4 g (7.9 mmol) of N-bromosuccinimide, iodine (a fraction) and dichloromethane were placed. The resulting mixture was allowed to react under reflux for 2 days.

After cooling, clean water was added to the reaction solution, and the resulting mixture was separated, followed by extraction. An organic phase was washed with clean water, an aqueous sodium thiosulfate solution and saturated saline, and dried with sodium sulfate, followed by concentration. Crystals obtained by the concentration were washed with methanol, and then dried under a reduced pressure, whereby 5.1 g of white solids were obtained. As a result of a FD-MS analysis, the resulting white solids were identified as intermediate e.

(2) Synthesis of Intermediate f

Intermediate f was synthesized by conducting a reaction in the same manner as in the synthesis of intermediate a, except that intermediate e was used instead of 1,6-dibromopyrene. Intermediate f was identified by a FD-MS analysis.

(3) Synthesis of Intermediate g Intermediate g was synthesized by conducting a reaction in the same manner as in the synthesis of intermediate b, except that intermediate f was used instead of intermediate a. Intermediate g was identified by a FD-MS analysis.

(4) Synthesis of D-3

D-3 was synthesized by conducting a reaction in the same manner as in the synthesis of D-1, except that intermediate g was used instead of intermediate b. D-3 was identified by a FD-MS analysis.

Example 4

Pyrene derivative (D-4) shown below was synthesized:

Intermediate a $\xrightarrow{D}$

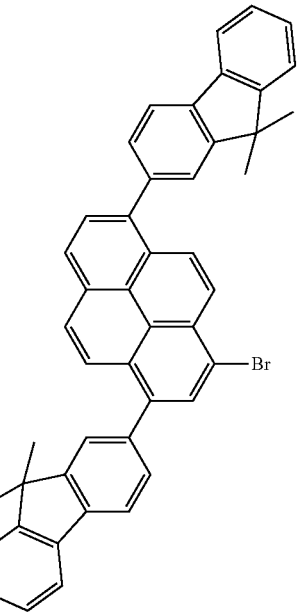

Intermediate h

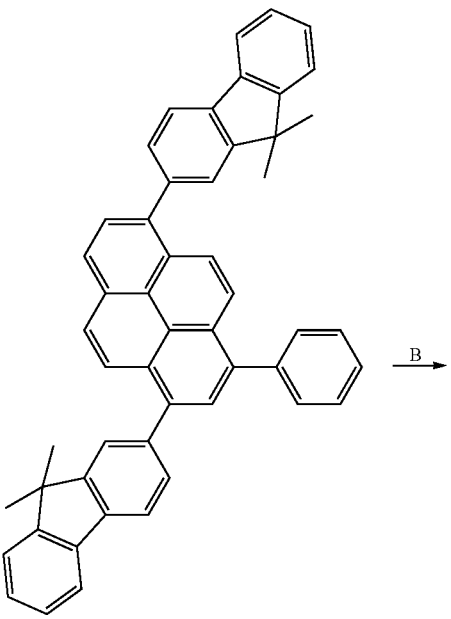

Intermediate i

-continued

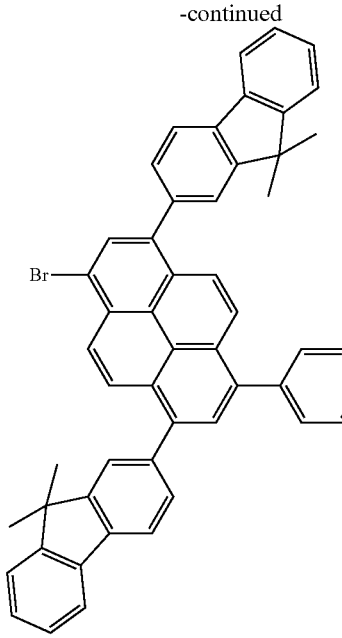

Intermediate j

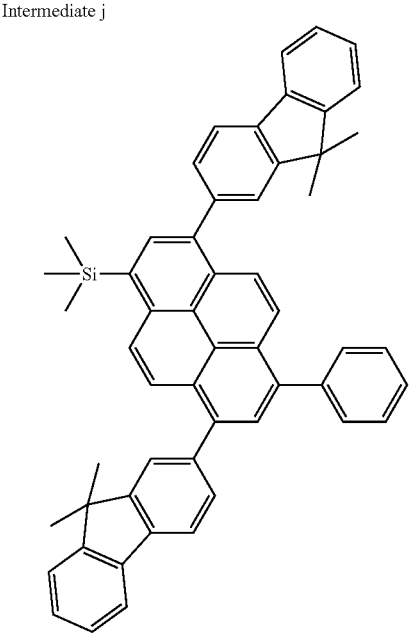

D-4

(1) Synthesis of Intermediate h
Intermediate h was synthesized by conducting a reaction in the same manner as in the synthesis of intermediate e, except that intermediate a was used instead of intermediate c. Intermediate h was identified by a FD-MS analysis.

(2) Synthesis of Intermediate i
Intermediate i was synthesized by conducting a reaction in the same manner as in the synthesis of intermediate a, except that intermediate h was used instead of 1,6-dibromopyrene and phenylboronic acid was used instead of 9,9-dimethylfluorene-2-ylboronic acid. Intermediate i was identified by a FD-MS analysis.

(3) Synthesis of Intermediate j
Intermediate j was synthesized by conducting a reaction in the same manner as in the synthesis of intermediate b, except that intermediate i was used instead of intermediate a. Intermediate j was identified by a FD-MS analysis.

(4) Synthesis of D-4
D-4 was synthesized by conducting a reaction in the same manner as in the synthesis of D-1, except that intermediate j was used instead of intermediate b. D-4 was identified by a FD-MS analysis.

Example 5

Pyrene derivative (D-5) shown below was synthesized:

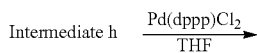

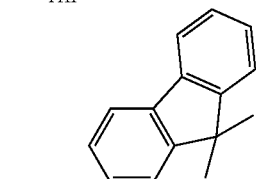

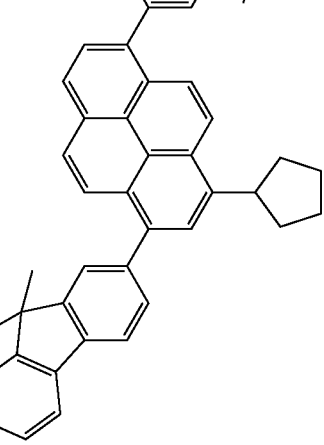

Intermediate k

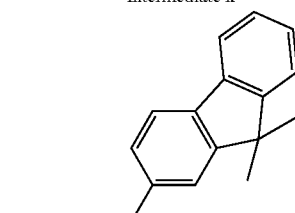

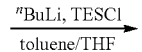

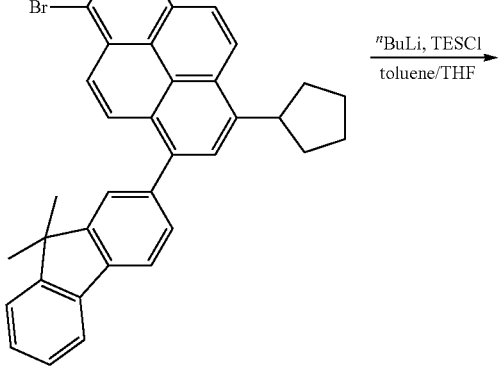

Intermediate l

-continued

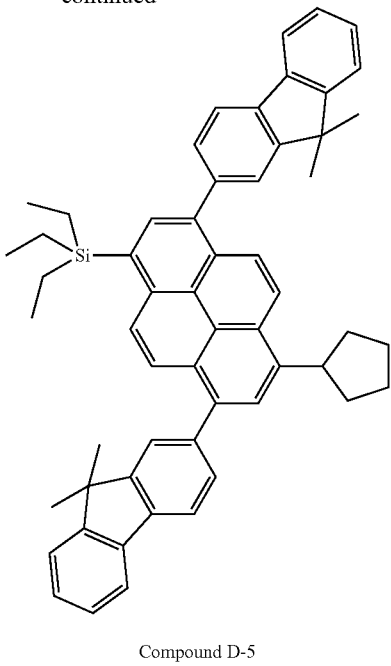

Compound D-5

(1) Synthesis of Intermediate k
Preparation of Grignard reagent: Under a flow of argon, in a 200 mL-recovery flask, 362 mg (15.1 mmol) of magnesium, iodine (a small amount), 2.2 g (15.1 mmol) of bromocyclopentane and tetrahydrofuran were placed and the resulting mixture was allowed to react at room temperature for 1 hour.

Under a flow of argon, in a 200 mL-recovery flask, 5 g (7.52 mmol) of intermediate h, 89 mg (0.15 mmol) of [1,3-bis (diphenylphosphino)propane]paradium(II)dichloride [Pd (dppp)Cl$_2$] and tetrahydrofuran were placed, the resulting mixture was heated to 50° C. The Grignard reagent prepared was added dropwise thereto for 50 minutes, and the resulting mixture was allowed to react at 50° C. for 7 hours.

After cooling, clean water and toluene were added to the reaction solution, and the resulting mixture was separated, followed by extraction. The extracted matter was washed with clean water and saturated saline, and dried with sodium sulfate, followed by concentration. Solids obtained were re-precipitated using toluene and methanol whereby 3.2 g of white solids were obtained.

As a result of a FD-MS analysis, the resulting white solids were identified as intermediate k.

(2) Synthesis of Intermediate l
Intermediate l was synthesized by conducting a reaction in the same manner as in the synthesis of intermediate b, except that intermediate k was used instead of intermediate a. Intermediate l was identified by a FD-MS analysis.

(3) Synthesis of D-5
D-5 was synthesized by conducting a reaction in the same manner as in the synthesis of D-1, except that intermediate l was used instead of intermediate b and triethylsilylchloride was used instead of trimethylsilylchloride. D-5 was identified by a FD-MS analysis.

Example 6

On a glass substrate of 25 mm by 75 mm by 1.1 mm thick, a 120 nm-thick transparent electrode formed of indium tin oxide was provided. This transparent electrode functioned as an anode. Subsequently, this glass substrate was cleaned by irradiating UV rays and ozone. The cleaned glass substrate was installed in a vacuum vapor deposition apparatus.

First, as the hole-injecting layer, HT-1 having the following structure was deposited in a thickness of 50 nm. Subsequently, on the thus formed film, N,N,N'N'-tetrakis(4-biphenyl)-4,4'-benzidine was deposited in a thickness of 45 nm as the hole-transporting layer. Then, 9,10-di(2-naphthyl)anthracene as a host material and pyrene derivative D-1 as a doping material were co-deposited in a mass ratio of 19:1, whereby an emitting layer with a thickness of 20 nm was formed.

On the thus formed emitting layer, ET-1 having the following structure was deposited in a thickness of 30 nm as the electron-injecting layer.

Subsequently, lithium fluoride was deposited in a thickness of 1 nm, followed by deposition of aluminum in a thickness of 150 nm, whereby an organic EL device was fabricated. The aluminum/lithium fluoride film functioned as a cathode.

For the thus fabricated organic EL device, the chromaticity, the external quantum yield at the time driving at a current density of 10 mA/cm$^2$ and the half life at an initial luminance of 150 cd/m$^2$ were measured. The results are shown in Table 1.

The 1931 CIE (x,y) chromaticity coordinates: measured by a spectroradiometer (CS-1000, produced by MINOLTA).

External quantum yield: Current having a current density of 10 mA/cm$^2$ was applied to the thus obtained organic EL device. Emission spectra thereof were measured with a spectroradiometer (CS-1000, produced by MINOLTA), and external quantum yield was calculated by the following equation (1):

$$E.Q.E. = \frac{N_P}{N_E} \times 100 \quad \text{Equation (1)}$$

$$= \frac{\frac{(\pi/10^9)\int \phi(\lambda)\cdot d\lambda}{hc}}{\frac{J/10}{e}} \times 100$$

$$= \frac{\frac{(\pi/10^9)\sum (\phi(\lambda)\cdot(\lambda))}{hc}}{\frac{J/10}{e}} \times 100(\%)$$

$N_P$: Number of photons
$N_E$: Number of electrons
$\pi$: Circular constant=3.1416
$\lambda$: Wavelength (nm)
$\phi$: Luminescence intensity (W/sr·m$^2$·nm)
h: Planck constant=6.63×10$^{-34}$ (J·s)
c: Light velocity=3×10$^8$ (m/s)
J: Current density (mA/cm$^2$)
e: Charge=1.6×10$^{-19}$ (C)

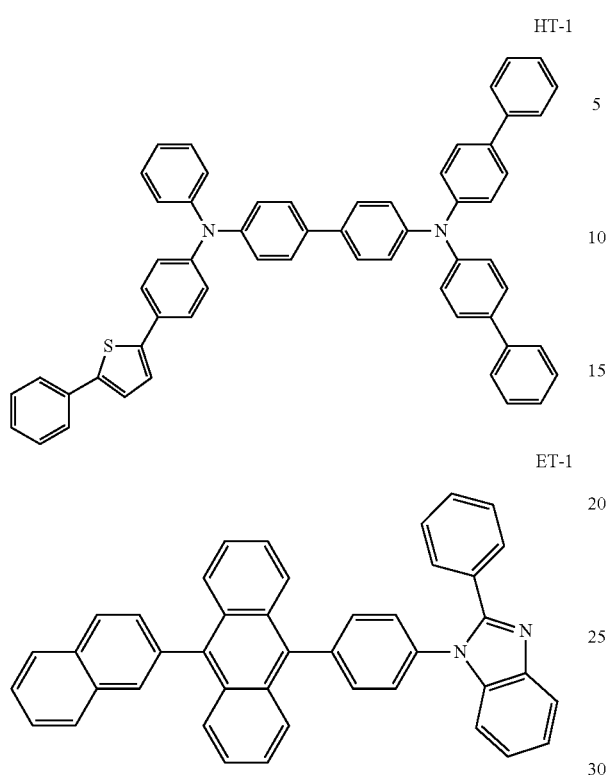

HT-1

ET-1

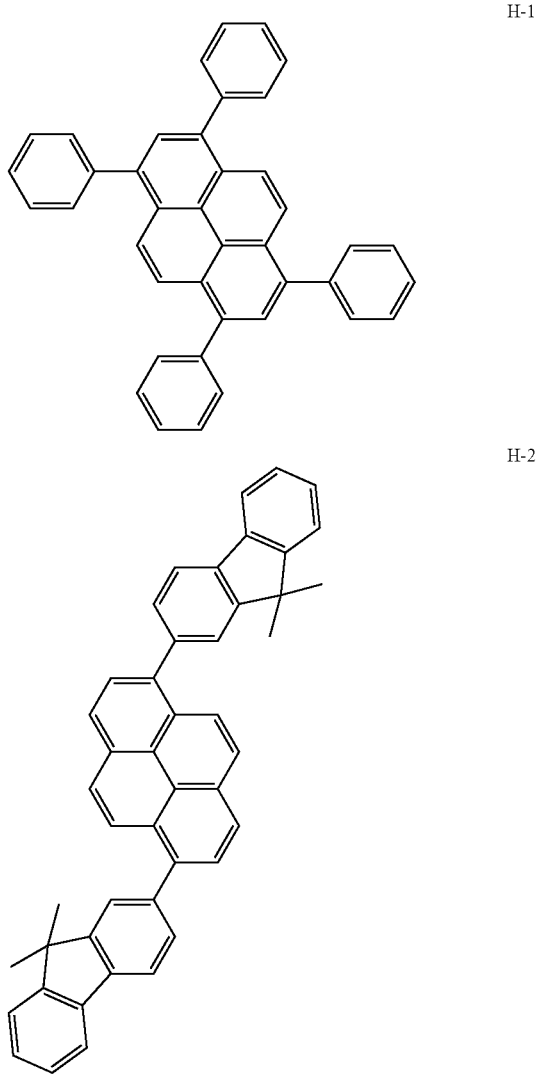

H-1

H-2

Example 7

An organic EL device was fabricated in the same manner as in Example 6, except that the following compound D-3 was used instead of D-1. The organic EL device thus obtained was evaluated in the same manner as in Example 6. The results are shown in Table 1.

Example 8

An organic EL device was fabricated in the same manner as in Example 6, except that the following compound D-4 was used instead of D-1. The organic EL device thus obtained was evaluated in the same manner as in Example 6. The results are shown in Table 1.

Example 9

An organic EL device was fabricated in the same manner as in Example 6, except that the following compound D-5 was used instead of D-1. The organic EL device thus obtained was evaluated in the same manner as in Example 6. The results are shown in Table 1.

Comparative Example 1

An organic EL device was fabricated in the same manner as in Example 6, except that the following compound H-1 was used instead of D-1. The organic EL device thus obtained was evaluated in the same manner as in Example 6. The results are shown in Table 1.

Comparative Example 2

An organic EL device was fabricated in the same manner as in Example 6, except that the following compound H-2 was used instead of D-1. The organic EL device thus obtained was evaluated in the same manner as in Example 6. The results are shown in Table 1.

|  | Dopant | CIEx | CIEy | EQE (%) | Life time (h) |
|---|---|---|---|---|---|
| Example 6 | D-1 | 0.147 | 0.066 | 6.8 | 7500 |
| Example 7 | D-3 | 0.149 | 0.068 | 6.9 | 7000 |
| Example 8 | D-4 | 0.148 | 0.072 | 6.9 | 8000 |
| Example 9 | D-5 | 0.147 | 0.067 | 6.7 | 7200 |
| Com. Example 1 | H-1 | 0.153 | 0.050 | 3.8 | 2500 |
| Com. Example 2 | H-2 | 0.153 | 0.054 | 4.2 | 2600 |

From the results of Examples 6 to 9, it can be understood that the luminous efficiency is improved since association in a part where association is most likely to occur is suppressed due to the presence of the group represented by the formula (2) in the pyrene skeleton. Further, it can also be understood that similar effects can be attained when only one group represented by the formula (2) is present in the molecule or when two groups represented by the formula (2) are present in the molecule.

INDUSTRIAL APPLICABILITY

An organic EL device using the pyrene derivative of the invention as a material for organic EL devices, particularly a material for an emitting material for organic EL devices is high in luminous efficiency.

The organic EL device of the invention is feasible and useful as a light source for a planar emitting body of a wall television or backlight of a display. The pyrene derivative of the invention can be used as a hole injecting/transporting material for an organic EL device, and further a carrier transporting material for an electrophotographic photoreceptor and organic semiconductor.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. A pyrene derivative represented by the following formula (1);

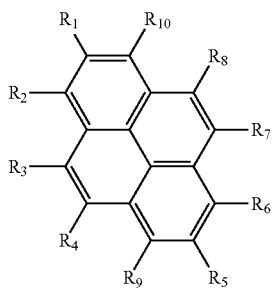

wherein $R_1$, $R_3$, $R_4$, $R_5$, $R_7$, and $R_8$ are a hydrogen atom, $R_2$ is a group represented by the following formula (2), $R_6$, $R_9$ and $R_{10}$ are independently a group represented by the formula (2) or a substituted or unsubstituted aryl group, and at least two of $R_6$, $R_9$ and $R_{10}$ are a substituted or unsubstituted aryl group, wherein the substituent of the substituted aryl group is a fluorine atom, a substituted silyl group, a cyano group, an unsubstituted aryl group, an alkyl group or a cycloalkyl group provided that in the case where only $R_2$ is a group represented by the formula (2), at least one of the substituted or unsubstituted aryl groups is an aryl group having 10 to 50 carbon atoms;

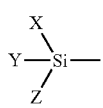

wherein X, Y and Z are independently a substituted or unsubstituted alkyl group, a substituted or unsubstituted aryl group or a substituted or unsubstituted alkoxy group.

2. The pyrene derivative of claim 1; wherein $R_9$ and $R_{10}$ are a substituted or unsubstituted aryl group.

3. The pyrene derivative of claim 2; wherein $R_6$ is a group represented by the formula (2).

4. An organic electroluminescence device comprising a pair of electrodes and an organic luminescent medium therebetween;
wherein the organic luminescent medium comprises one or more organic compound layers comprising an emitting layer, and the organic luminescent medium comprises at least one pyrene derivative of claim 1.

5. The organic electroluminescence device of claim 4; wherein the emitting layer comprises the pyrene derivative.

6. The organic electroluminescence device of claim 5; wherein the content of the pyrene derivative in the emitting layer is 0.01 to 20 mass %.

7. The pyrene derivative of claim 1; wherein the formula (1) is selected from formulae (3), (5), and (7)

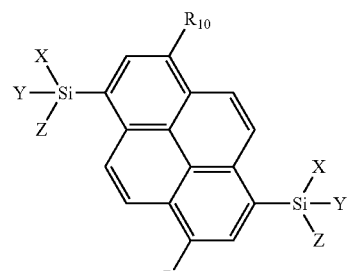

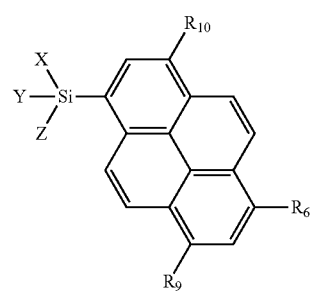

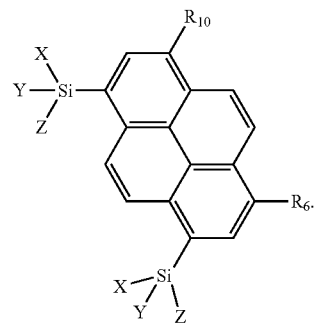

8. The pyrene derivative claim of 1; wherein X, Y and Z are independently a substituted or unsubstituted alkyl group having 1 to 20 carbon atoms, a substituted or unsubstituted aryl group having 6 to 50 ring carbon atoms or a substituted or unsubstituted alkoxy group represented by the following formula (9);

—OY'     (9)

wherein Y' is a substituted or unsubstituted alkyl group having 1 to 20 carbon atoms.

9. The pyrene derivative of claim 1; wherein $R_6$ is a substituted or unsubstituted aryl group.

10. The pyrene derivative of claim 1; wherein $R_9$ and $R_{10}$ are independently a substituted or unsubstituted phenyl group, a substituted or unsubstituted naphthyl group, a substituted or unsubstituted fluorenyl group, a substituted or unsubstituted phenanthryl group, a substituted or unsubstituted anthracenyl group, a substituted or unsubstituted biphenyl group, or a substituted or unsubstituted terphenyl group.

* * * * *